United States Patent [19]

Hoffman

[11] 4,257,863

[45] Mar. 24, 1981

[54] GAS SENSORS AND METHOD OF MAKING SUCH SENSORS

[75] Inventor: John W. Hoffman, Beecroft, Australia

[73] Assignee: The Broken Hill Proprietary Company Limited, Melbourne, Australia

[21] Appl. No.: 47,691

[22] Filed: Jun. 12, 1979

[51] Int. Cl.³ .............................................. G01N 27/58
[52] U.S. Cl. ............................. 204/195 S; 427/123; 427/125; 427/126.1
[58] Field of Search .............. 204/195 S, 15; 427/123, 427/125, 126

[56] References Cited

U.S. PATENT DOCUMENTS

| | | | |
|---|---|---|---|
| 3,468,780 | 9/1969 | Fischer | 204/195 S |
| 3,503,809 | 3/1970 | Spacil | 204/195 S |
| 4,021,326 | 5/1977 | Pollner et al. | 204/195 S |
| 4,107,018 | 8/1978 | Bode et al. | 204/195 S |
| 4,164,462 | 8/1979 | Ichikawa et al. | 204/195 S |

FOREIGN PATENT DOCUMENTS 1507008  4/1978  United Kingdom .

*Primary Examiner*—G. L. Kaplan
*Attorney, Agent, or Firm*—Cushman, Darby & Cushman

[57] ABSTRACT

This specification discloses an improved electrochemical gas sensor comprising a closed end stabilized zirconia tube to which a porous layer of powdered zirconia is applied so as to be intimately bonded to the tube, and a layer of porous electrode material which in the use of the sensor is exposed to the gases to be analyzed. The provision of the porous layer of powdered zirconia substantially improves the bonding of the outer electrode layer to the zirconia tube. In the preferred embodiment a further powdered zirconia layer is applied to the electrode to protect the electrode and to inhibit chemical contamination of the zirconia/electrode interface of the sensor.

12 Claims, No Drawings

GAS SENSORS AND METHOD OF MAKING SUCH SENSORS

This invention relates to sensors suitable for use in the analysis of gases such as oxygen and including a solid ceramic electrolyte member and an electrode of a suitable noble metal such as platinum, palladium, gold or silver.

In our Australian Pat. No. 493,408, we disclose a method of applying an electrode to a solid ceramic electrolyte member, which method overcomes some of the disadvantages of the prior art electrodes as outlined in the specification of the patent.

It has now been discovered that electrodes of the general type described in the above patent are prone to chemical contamination from their working environment; for example the electrodes tend to pick-up iron from the work tube in which the sensor is located in use. The iron is found to penetrate through the porous electrode layer of the sensor and deposits at the electrolyte/electrode interface where it causes a reaction which seriously affects the response characteristics of the sensor. Sensors having an iron pick-up problem are found to have unacceptably long response times.

Experiments revealed that such chemical contamination could be at least substantially reduced by the application of porous coating or layer of material intimately bonded to the electrode layer of the sensor and with which chemical species reacted to prevent reactions taking place at the electrolyte/electrode interface of the sensor. The application of such layers can be achieved by known thermal deposition processes such as plasma spraying. However, it was found that the thermal shock resulting from such deposition processes often caused the electrode to peel or flake off and accordingly a more secure method of bonding the electrode layer to the electrolyte substrate was required.

It is an object of the present invention to provide a gas sensor of the general type referred to above in which the electrode is more securely bonded to the substrate.

The invention provides an electrochemical gas sensor comprising a solid electrolyte substrate and an outer porous electrode layer of electrode metal which in use of the sensor element is exposed to gases to be analysed, the improvement which comprises an intermediate porous layer of at least compatible electrolyte material intimately bonded to said substrate and to which the outer electrode layer is in turn intimately bonded.

It has been found that the provision of an intermediate layer of electrolyte material not only increases the adherence of the electrode layer to the substrate but also improves the response time of the sensor.

In a particularly preferred form of the invention, the electrode layer is provided with a porous coating or layer of material intimately bonded to said electrode layer and with which chemical species react to substantially prevent reactions taking place at the electrolyte/electrode interface of the sensor.

The coating is preferably of the same material as said intermediate layer although the material does not act as an electrolyte. The porous layer not only overcomes the problems caused by chemical contamination but also protects the electrode layer against erosion and other damage caused by the environment in which the sensor is used.

Where the solid electrolyte substrate is zirconia, it is preferred that the two coatings are of a similar or at least compatible ceramic electrolyte material such as calcia stabilized zirconia. However, other ceramic or heat resistant materials, such as alumina, may be suitable as the outer coating provided it bonds to the electrode and the necessary chemical contamination reaction takes place other than at the main electrolyte/electrode interface.

The two electrolyte layers are preferably from 0.02 mm to 0.5 mm thick, preferably from 0.03 mm to 0.06 mm. The lower limit of the above range represents the approximate minimum thickness that can be applied with one pass of a plasma coating gun while the other limit is dictated by the thermal shock that can be withstood by the sensor being coated and the cost of the coating. The electrode layer is preferably platinum from 0.005 mm to 0.5 mm thick, preferably from 0.03 mm to 0.06 mm. The range of thicknesses and the method of application of the electrode layer are substantially as described in the specification of the above patent the disclosure of which is incorporated into the present specification by cross-reference.

One preferred method of manufacturing or repairing a gas sensor in accordance with the preferred form of the invention will now be described. The method is described in relation to closed end zirconia sheaths of the type well known in the art although it will be appreciated that the method is equally applicable to other electrolyte materials and configurations.

(1) The zirconia sheath is examined for gas-tightness by filling with alcohol. If a hole is present, it will show as a dark hairline crack.

(2) The open end of the sheath is masked approximately 4 cm from the end with PVC tape. This enables a leak-proof seal to be subsequently obtained in this region when the sheath is installed for use.

(3) The sheath is then grit blasted with a suitable material such as Metcolite C. In performing the grit blasting, several factors must be borne in mind:

(I) The abrasive should be clean and dust free.

(II) Excessive air pressure should be avoided as this may cause pitting. Air pressures of the order of 500 to 700 KPa have been found to be suitable.

(III) The grit blasting should be conducted as uniformly as possible over the surface of the sheath.

(IV) After the grit blasting has been performed, care should be taken not to handle the clean surface of the sheath. It is advisable to use a clean cotton cloth (non-synthetic) for handling purposes.

(4) The sheath is once again examined for gas-tightness.

(5) The masking tape is removed and the sheath is placed in a cold heating block whereupon the sheath is preheated to a temperature of approximately 250° C.

(6) The sheath is positioned on a mandrel for spraying; an aluminium rod of dimensions 5 cm long by 2 cm in diameter with a 4 cm by 1 cm bore is found to be suitable as the mandrel.

(7) Prior to fitting the sheath, the mandrel is preheated for approximately 20 seconds by means of a plasma gun located approximately 25 to 30 cm from the mandrel with the mandrel rotating. It has been found that a Metco 3M 40 Kilowatt plasma unit operated in accordance with the recommendations in the Metco handbook is suitable for the coating operation.

(8) The sheath is removed from the heating block and placed on the preheated mandrel and the mandrel rotated at about 20 rpm.

(9) A plasma gun of the above type connected to a suitable stabilized zirconia powder supply is held at approximately 15 to 30 cm from the sheath and one pass is made from the closed end of the sheath. The sheath is observed closely for any powder adherence which can be detected by a lighter colour appearance on the sheath. If no powder adherence is detected, the gun is moved closer to the sheath until the colour change has been observed. Four passes are then made with the gun starting at the closed end. At the completion of the fourth pass the powder feed is switched off and the gun held at an angle of 90° to the closed end for approximately 2 seconds. Sufficient powder remains in the feed line to the gun to coat this area of the sheath.

(10) The sheath is removed from the mandrel and is placed carefully in the heating block where it is maintained at a temperature of 250° C. for approximately 30 minutes. The heating block is then turned off and the sheath allowed to cool to room temperature over approximately 3 hours.

(11) The electrolyte coated sheath is then coated with a layer of porous platinum in accordance with the procedure laid down in Australian Pat. No. 493,408 (84415/75). When the platinum coating has been fired a further coating of electrolyte is applied by the same procedure from the preheating step as described above.

A sensor manufactured by the method described above substantially avoids the problems associated with chemical contamination and also has a response time which is superior to that of the prior art sensors. Experiments have shown that the response time of sensors of the type described in the above Australian Patent is improved by a factor of about ten. Accordingly, sensors embodying the invention have quite substantial advantages over the prior art sensors.

I claim:

1. In a sensor to determine oxygen concentration in gases comprising a tubular solid electrolyte substrate and an outer porous circumferential electrode layer of electrode metal which in use of the sensor element is exposed to gases to be analyzed, the improvement which comprises an intermediate porous layer of compatible electrolyte material intimately bonded to said substrate and to which the outer electrode layer is in turn intimately bonded, and a further porous layer of compatible electrolyte material intimately bonded to said electrode layer and with which chemical species react to substantially prevent reactions taking place at the electrolyte/electrode interface of the sensor.

2. The gas sensor of claim 1, wherein said intermediate electrolyte layer is from about 0.02 mm to about 0.5 mm thick.

3. The gas sensor of claim 2, wherein said intermediate electrolyte layer is from about 0.03 mm to about 0.06 mm thick.

4. The gas sensor of claim 3, wherein said substrate is stabilized zirconia and said intermediate electrolyte layer is stabilized zirconia thermally deposited on said solid electrolyte substrate.

5. The gas sensor of claim 1, wherein said further layer is of the same material as said intermediate electrolyte layer and is of similar thickness.

6. The gas sensor of claim 1, wherein said electrode layer is of a noble metal from about 0.005 mm to about 0.5 mm thick.

7. A method of manufacturing a gas sensor comprising the steps of cleaning the surface of a tubular solid electrolyte substrate, intimately bonding a porous layer of compatible electrolyte material to said substrate, intimately bonding a porous circumferential layer of electrode metal to said electrolyte layer, and intimately bonding a porous layer of compatible electrolyte material to said electrode layer, and with which chemical species react to substantially prevent reactions taking place at the electrolyte/electrode interface of the sensor.

8. The method of claim 7, wherein said electrolyte layer is thermally deposited to a thickness of from about 0.03 mm to about 0.06 mm and said electrode layer is intimately bonded to said electrolyte layer by firing a noble metal paste from about 0.005 mm to about 0.5 mm thick.

9. An electrochemical gas sensor element comprising: a tubular solid electrolyte substrate; a porous layer of the same electrolyte material thermally sprayed on and bonded to the substrate; a porous circumferential layer of electrode metal deposited on and bonded to said porous layer of electrolyte material whereby said metal layer is strongly adhered to said substrate so as to resist peeling from said substrate by thermal shock, said metal layer in use of the sensor element being exposed to gases to be analyzed; and a further porous layer of the same electrolyte material thermally sprayed on and bonded to the metal layer, said further layer being capable of reacting with chemical species to substantially prevent reactions taking place at the substrate/electrode metal interface of the sensor element.

10. A gas sensor as in claim 9 wherein the two porous electrolyte layers are 0.02 mm to 0.5 mm thick and wherein the electrode metal layer is 0.005 mm to 0.5 mm thick.

11. A method of manufacturing a gas sensor element comprising: cleaning the surface of a tubular solid electrolyte substrate, thermally spraying and intimately bonding a porous layer of the same electrolyte material on to said substrate; depositing and intimately bonding a porous circumferential layer of electrode metal on to said porous electrolyte layer to strongly adhere said metal layer to said substrate so as to resist peeling of said metal layer from said substrate by thermal shock; and thermally spraying and intimately bonding a porous layer of the same electrolyte material to said metal layer.

12. A method as in claim 11 wherein the two porous electrolyte layers are 0.02 mm to 0.5 mm thick and wherein the electrode metal layer is 0.005 mm to 0.5 mm thick.

* * * * *

UNITED STATES PATENT AND TRADEMARK OFFICE
CERTIFICATE OF CORRECTION

PATENT NO. : 4,257,863
DATED : March 24, 1981
INVENTOR(S) : John William Hoffman It is certified that error appears in the above—identified patent and that said Letters Patent is hereby corrected as shown below:

On the front page format, after paragraph "[21]",
insert: --[30] Foreign Application Priority Data
      June 12, 1978   Australia............PD 4694--.

Signed and Sealed this

Third Day of November 1981

[SEAL]

*Attest:*

*Attesting Officer*

GERALD J. MOSSINGHOFF

*Commissioner of Patents and Trademarks*